US007005558B1

(12) United States Patent
Johansson et al.

(10) Patent No.: US 7,005,558 B1
(45) Date of Patent: *Feb. 28, 2006

(54) APERTURED COVERING SHEET FOR AN ABSORBENT ARTICLE AND A METHOD OF PRODUCING THE COVERING SHEET

(75) Inventors: Anette Johansson, Göteborg (SE); Agneta Thorén, Landvetter (SE)

(73) Assignee: SCA Hygiene Products AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,520

(22) PCT Filed: Apr. 25, 1997

(86) PCT No.: PCT/SE97/00696

§ 371 (c)(1),
(2), (4) Date: Sep. 2, 1999

(87) PCT Pub. No.: WO97/40793

PCT Pub. Date: Nov. 6, 1997

(30) Foreign Application Priority Data

May 2, 1996 (SE) .................................. 9601681

(51) Int. Cl.
*A61F 13/15* (2006.01)

(52) U.S. Cl. .................. 604/383; 604/370; 604/378
(58) Field of Classification Search .............. 604/383, 604/366, 367, 370, 385.08; 428/131–140
See application file for complete search history.

(56) References Cited

U.S. PATENT DOCUMENTS

| 3,344,789 | A | * | 10/1967 | Arnold et al. | 128/287 |
|---|---|---|---|---|---|
| 3,403,681 | A | * | 10/1968 | Hoey et al. | 128/290 |
| 3,703,897 | A | * | 11/1972 | Mack et al. | 128/156 |
| 3,814,101 | A | * | 6/1974 | Kozak | 128/287 |
| 3,886,941 | A | * | 6/1975 | Duane et al. | 128/287 |
| 3,927,673 | A | * | 12/1975 | Taylor | 128/287 |
| 3,929,135 | A | * | 12/1975 | Thompson | 128/287 |
| 4,626,254 | A | * | 12/1986 | Widlund et al. | 604/383 |
| 4,798,603 | A | * | 1/1989 | Meyer et al. | 604/378 |
| 5,188,625 | A | * | 2/1993 | Van Iten et al. | 604/383 |
| 5,281,208 | A | * | 1/1994 | Thompson et al. | 604/378 |
| 5,415,640 | A | * | 5/1995 | Kirby et al. | 604/366 |
| 5,478,335 | A | * | 12/1995 | Colbert | 604/383 |
| 5,591,149 | A | * | 1/1997 | Cree et al. | 604/378 |
| 5,613,960 | A | * | 3/1997 | Mizutani | 604/365 |
| 5,746,729 | A | * | 5/1998 | Wada et al. | 604/378 |
| 5,814,389 | A | * | 9/1998 | Giacometti | 428/132 |

(Continued)

FOREIGN PATENT DOCUMENTS

DE 26 14 160 10/1977

(Continued)

*Primary Examiner*—Tatyana Zalukaeva
*Assistant Examiner*—C. Lynne Anderson
(74) *Attorney, Agent, or Firm*—Buchanan Ingersoll PC

(57) ABSTRACT

A liquid permeable covering sheet of an absorbent article such as a diaper, an incontinence protector, or a sanitary napkin which comprises an apertured textile material. The covering sheet has a plurality of holes, each of which is surrounded by an essentially liquid-type edge. The invention further comprises an absorbent article with a covering sheet according to the invention. A method of making the covering sheet by causing heated needles to penetrate a textile material layer comprising at one thermoplastic component is also covered by the invention.

10 Claims, 4 Drawing Sheets

U.S. PATENT DOCUMENTS

| | | | |
|---|---|---|---|
| 5,916,661 A * | 6/1999 | Benson et al. | 428/131 |
| 5,986,167 A * | 11/1999 | Arteman et al. | 604/380 |
| 6,039,906 A * | 3/2000 | Sageser et al. | 264/156 |
| 6,168,849 B1 * | 1/2001 | Braverman et al. | 156/148 |
| 6,452,064 B1 * | 9/2002 | Thoren et al. | 604/383 |

FOREIGN PATENT DOCUMENTS

| | | |
|---|---|---|
| EP | 0 080 383 | 6/1983 |
| EP | 0 164 740 | 12/1985 |
| EP | 0 214 608 | 3/1987 |
| EP | 0 214 608 A2 | 3/1987 |
| EP | 0 235 309 A1 | 9/1987 |
| EP | 0 272 683 A2 | 6/1988 |
| EP | 0 235 309 B1 | 10/1989 |
| EP | 0 409 535 A1 | 1/1991 |
| EP | 0 409 535 B1 | 3/1994 |
| EP | 0 598 970 | 6/1994 |
| WO | WO 94/10956 | 5/1994 |
| WO | WO 96/20664 | 7/1996 |

* cited by examiner

APERTURED COVERING SHEET FOR AN ABSORBENT ARTICLE AND A METHOD OF PRODUCING THE COVERING SHEET

TECHNICAL FIELD

The present invention refers to a liquid permeable covering sheet for an absorbent article, such as a diaper, an incontinence protector, a sanitary napkin or the like, which comprises an apertured textile material. The invention also refers to an absorbent article provided with the covering sheet, and a method of producing the covering sheet.

BACKGROUND OF THE INVENTION

For liquid permeable covering layers for absorbent articles of this kind, which during use are intended to be in contact with the body of the user, there are high demands for softness as well as dryness.

It has, however, proven difficult to achieve a liquid permeable covering layer with a soft and textile-like surface which remains dry even after repeated wetting, when the covering layer is used on an absorbent article.

The use of non-woven fibrous fabrics, so-called non-woven materials, for creating a soft and smooth surface on an absorbent article has been known for a long time. Providing the non-woven material with apertures in order to more rapidly transfer liquid through the surface material down to an underlying absorbent material layer, is also known. When making the apertures, openings are created in the material, which are larger than the space between the fibres in the non-woven material.

One such apertured non-woven material is previously known from EP 235,309. The apertured non-woven material consists of a spunlace material with a high content of hydrophobic fibres. In a spunlace process, holes are made in a fibrous material by treating the material with water jets which are sprayed against the material at very high pressure. The spunlace material constitutes one of two layers in a surface material laminate and is intended to be the layer which, during use, is closest to the user. The purpose is that the liquid will be guided through the holes in the spunlace material down to the underlying layer. The spunlace material has a higher content of hydrophobic fibres than the underlying material layer in the surface laminate. The fibres of the uppermost spunlace layer consist of 70% hydrophobic fibres and 30% hydrophilic fibres, while the underlying material layer consists of equal amounts of hydrophobic and hydrophilic fibres. Thus, the underlying layer thus has the ability to drain liquid from the upper layer.

However, a problem with the material described in EP 235,309 is that holes which are formed by water jets become irregular both in size and shape, and have fibres which protrude from the edges of the holes around and in the holes. These protruding fibres decrease the area of the holes, and also, due to capillary effects, wick liquid into the material between the holes. The protruding fibre ends and the irregular size and shape of the holes significantly increase the risk of liquid remaining in the layer after wetting. Since a very small amount of liquid is sufficient for the surface material to be perceived as wet, this is of course a significant disadvantage of the known surface material.

A similar surface material is described in EP 272,683. This publication also concerns an apertured covering layer of non-woven material. In the vicinity of the holes, which have been formed by perforating the non-woven material, there are relatively loose fibres which are intended to function as transport canals for the liquid down to an underlying non-woven layer of the so called meltblown type. As long as the fibres of the perforated layer are arranged in such a way that they lead the liquid towards the underlying layer, the described surface material works. It is, however, a well known fact that a non-woven material consists of irregularly formed fibres which are difficult to arrange in any particular direction. This means that fibre capillaries which are intended to transport liquid to the underlying layer will also spread liquid in a horizontal direction across the surface of the non-woven material. For this reason, some of the liquid will remain in the surface material after wetting, and the user of an article provided with the surface material will experience the surface of the article as being wet and unpleasant against the skin.

A further problem with the above described non-woven materials is that it is difficult to achieve a particular, well defined, hole size. It is, for instance from EP 409,535 well known that the dimension of the holes in a perforated material is crucial in order to achieve optimal permeability for the liquid. For non-woven materials having some areas with a dense fibre structure and other areas with a sparse fibre structure, this means that it is difficult to obtain a uniform hole size. This is due to the fact that the holes in the dense fibre areas become smaller, since they are surrounded by more fibres.

Further, the perforated non-woven materials in previously known surface materials further have a relatively low tensile strength, since the described hole-making process weakens the material. Since it is important that the strength of the material is such that there is no risk that it will break, either during the hole-making process, during the manufacturing of the absorbent article, or during use of the finished absorbent article, evidently the weakening of the known materials is a problem.

In EP 214,608 holes are made in a non-woven material using warm needles which heat the non-woven material to a temperature which is slightly below the melting point of the material. The holes which are thus made in the material are surrounded by an edge which has a densified fibre structure. With a material with holes made in this way, the above mentioned problems with varying hole sizes and weakening of the material have been solved to a certain extent. However, the problem of avoiding liquid being spread out in the non-woven material and remaining in its fibre structure still remains. The denser fibre structure surrounding the holes is intended to absorb liquid thereby wicking the liquid further through the holes in to an underlying material layer. There is, however, a risk that some liquid will remain in the denser hydrophilic fibre structure around the holes. Liquid can also spread horizontally in the plane of the non-woven material via the fibre capillaries in the non-woven material. Since the non-woven material during use is in direct contact with the skin of the user, this is of course extremely undesireable.

SUMMARY OF THE INVENTION

The problem of achieving a liquid permeable surface layer for absorbent articles, which surface layer is soft and comfortable against the skin, but still has a high surface dryness, has essentially been solved with the present invention.

By means of the invention an apertured covering layer of non-woven material has thus been achieved which significantly reduces the risk of wetting of the skin of the user during use.

An apertured covering layer of non-woven material according to the invention is characterized primarily in that the textile material has a plurality of holes, each hole being surrounded by an essentially liquid-tight edge.

In this context, the term textile material refers to a material in layer form, which has been manufactured from natural or synthetic textile fibres, such as for example cotton, rayon, polypropylene, polyester, polyethylene, bi-component fibres, etc.

According to a preferred embodiment, the covering material surrounding the holes comprises a thermoplastic material which has been melted, and thus forms the liquid-tight edge.

The holes can be made using warm needles, in which case the liquid-tight edges around the holes are made simultaneously with the holes.

In an alternative embodiment, the holes in the covering layer have instead been made ultrasonically.

Since the holes are surrounded by a melted edge which is liquid-tight and free from protruding fibres, a well defined hole size can be obtained. The optimal hole size varies with the use of the surface layer. For example menstrual fluid and urine have completely different surface energies and different rheological qualities, which means that the design of the surface layer must be adapted accordingly. However, in a covering material according to the invention, the form and size of the holes deviate minimally from the intended optimal form and size which is determined with regard to the intended use of the covering material. In accordance with the invention, it is therefore possible to create high performance covering materials with a high degree of accuracy and repeatability for a number of different absorption applications.

A non-woven material of the spunbond type has proven to perform especially well as surface material according to the invention. The term spunbond refers to a thermobonded material of endless, randomized fibres. It is, however, possible to use other types of non-woven materials. Other types of non-woven materials which are not as strong, for example carded materials, which have a lesser strength in the transverse direction of the material than in its longitudinal direction may however also be used, since the continuous edge around the holes provides the material with increased tensile strength. It is thus possible, according to the invention, to use carded non-woven materials, meltblown materials, etc. A meltblown material is a non-woven material which has been formed by blowing an extruded melted plastic against a surface. Furthermore, different woven, knitted, crocheted or plaited textile materials can be used in accordance with the invention.

According to one embodiment of the invention the covering layer has holes of varying size. The holes can be evenly distributed over the surface of the covering layer, or be more closely spaced in certain areas.

According to another embodiment of the invention, the covering layer comprises at least two layers of material.

In such an application a first layer of material is preferably more hydrophilic than a second layer of material in the covering layer. It can furthermore be advantageous if the liquid-tight edge around the holes in the covering layer is provided only in the first layer of material.

According to yet another embodiment, the covering layer can be laminated to an unperforated liquid transfer layer, which, when the covering layer is attached to an absorbent article, serves as liquid transferring means between the covering layer and the absorption body of the article.

The invention also includes an absorbent article, such as for example a sanitary napkin, a diaper, an incontinence protector etc, which comprises an absorption body enclosed in a cover, where at least a section of the cover consists of a liquid permeable covering layer of a textile apertured material. The article according to the invention is mainly characterized by having a plurality of apertures in the apertured covering layer, each aperture being surrounded by a liquid impermeable edge.

In one embodiment the article has two end-portions and a crotch-portion positioned between the end-portions wherein the liquid permeable covering layer is provided with holes arranged in the crotch-portion which have a larger surface than holes made in the covering layer at either of the end-portions.

In another embodiment, the article has two longitudinal side edges, where one side area along each side edge is provided with holes which have a smaller dimension and/or are more sparsely arranged than holes arranged inside the edge areas in the crotch-portion of the article.

Furthermore, the invention comprises a method of forming an apertured textile covering layer wherein heated needles are arranged to penetrate a textile material layer comprising at least one thermoplastic component, during which procedure the temperature of the needles exceeds the melting temperature of the thermoplastic component. The main characteristic of this method is that the thermoplastic component comprises at least 55 weight % of the material in the textile material layer, and in that the heated needles are arranged to melt the thermoplastic component in the immediate vicinity of the needles, after which the needles are removed and the melted material is solidified to form an essentially liquid impermeable edge around each of the holes made.

A covering material according to the invention obtains an increased tensile strength in the apertured textile material. Thus, the starting material for the production of the apertured covering material can be chosen more freely than has been possible with earlier known perforated non-woven materials.

The liquid-proof edges around the holes also imply that liquid can not spread horizontally from the holes through fibre capillaries in the non-woven material. When the covering material is attached to an absorbent body, the liquid will instead pass through the holes and can be absorbed by the absorption body of the article.

BRIEF DESCRIPTION OF THE DRAWINGS

The invention will be described in the following in further detail with reference to the embodiments shown in the attached drawings.

Figure 1:
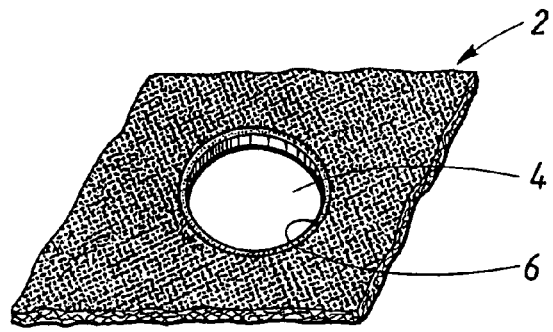
FIG. 1 shows an apertured non-woven material with melted edges around the holes.

The liquid permeable covering sheet 2, shown in FIG. 1, consists of one or several layers, which together form the covering sheet 2. The different layers in the covering sheet 2 can be non-woven materials of different types or composition. It is, however, also possible to use one or several layers of plastic film, net material, woven or knitted textile material etc. If the covering sheet 2 consists of more than one layer, it is however essential to the invention that at least that layer which is intended to face the user during use of the covering sheet 2 as a liquid permeable surface sheet of an absorbent article, consists of a textile material.

Examples of possible textile materials are woven or knitted fabrics, and so-called non-woven materials, i.e. non-woven fibrous fabrics. In the following, the covering sheet 2 will for reasons of simplicity be described as though it consists of only one layer of textile nature. It should however be understood in connection with all the described embodiments that the covering sheet 2 may consist of more than one layer of material.

The textile material provides the covering sheet 2 with a soft and pleasant surface, which is not abrasive or otherwise irritating for the skin. The textile material comprises at least one thermoplastic component, which can be in the form of whole fibres, or as one component in a so-called bi-component fibre. Thermoplastic materials suitable for the purpose are polyethylene, polypropylene or polyester. The thermoplastic component constitutes at least 55 weight % of the textile material, at least in the area which is perforated in accordance with the invention. Preferably the thermoplastic component constitutes at least 70 weight % of the textile material. It is, furthermore, possible to use textile materials which consist solely of a thermoplastic material.

The covering sheet 2 further has a plurality of through-going holes 4, which have been made by penetrating the sheet 2 with heated needles. During this procedure, the temperature of the needles has been such that it has exceeded the melting temperature of the thermoplastic component in the textile material. The amount of material which melts during penetration of the covering layer is high enough to provide the finished material with an essentially liquid impermeable edge 6 around the hole. The liquid-tight edge 6 increases the tensile strength of the covering layer and prevents liquid from spreading from the edge 6 of the hole, across the surface of the covering layer 2. This liquid barrier effect is due to the fact that there are no free fibre ends around the holes which might capture the liquid and, by capillary action, wick it in the wrong direction, away from the hole 4.

Since the material around the holes 4 is melted in at least a first layer of the covering sheet 2, this implies that the edges 6 of the holes, inside the holes, are comparatively smooth, at least through a part of the thickness of the material in the covering sheet 2. For this reason, the edges 6 of the holes have considerably less restricting influence on a flow of liquid through the covering sheet 2 than is the case with earlier known covering layers of perforated non-woven materials. Passage of liquid through the covering sheet 2 according to the invention can thus take place rapidly and relatively unhindered.

Figure 2:
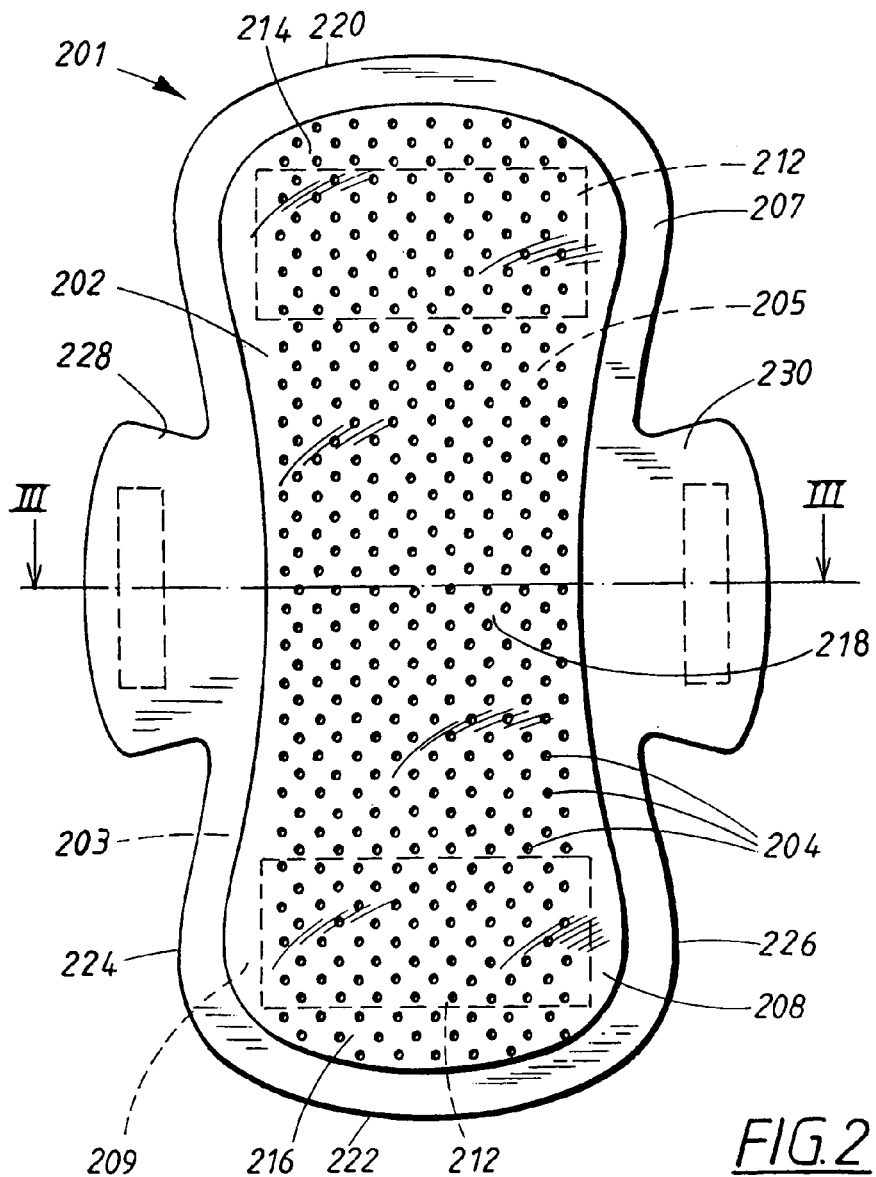
FIG. 2 shows a sanitary napkin with a liquid permeable covering layer according to the invention, seen from that side which during use is intended to face the user.
Figure 3:
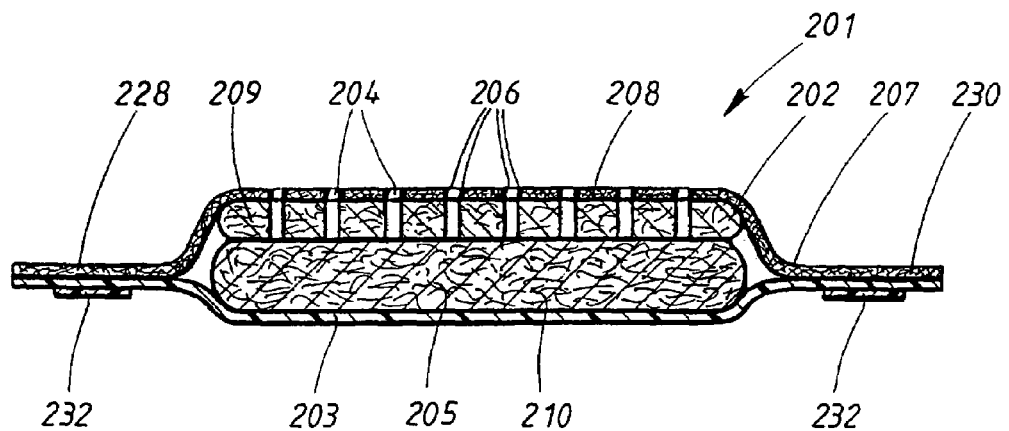
FIG. 3 shows a cross-section through the sanitary napkin of FIG. 2.

The sanitary napkin 201 of FIGS. 2 and 3 comprises a first liquid permeable covering sheet 202 according to the invention, a liquid impermeable covering sheet 203, and an absorption body 205 enclosed between the covering sheets 202,203. The liquid impermeable covering sheet 203 may consist of a liquid-tight plastic film, a non-woven layer which has been coated with a liquid impermeable material, or some other flexible material layer which is resistant to penetration of liquid. It is generally an advantage if the liquid impermeable covering sheet 203 has a certain degree of breathability, i.e. it allows passage of water vapour. The two covering sheets 202,203 have a somewhat larger extension in the plane than the absorption body 205, and extend somewhat outside the edges of the absorption body 205, around its entire circumference. The surface sheets 202,203 are connected within the protruding parts 207, for example by glueing, or welding with heat or ultrasonically.

The absorption body 205 usually consists of one or several layers of cellulose fibres, for example fluffed cellulose pulp. An example of an absorbent structure suitable for this purpose is described in WO 94/10956, which publication describes an absorbent material, which is cut from a travelling material web, without previous defibering and mat forming. The material increases the surface dryness of the finished absorbent article, which is an advantage particularly when the liquid permeable covering layer 202 has a textile material layer closest to the user.

The absorbtion body 205 may, in addition to cellulose fibres, also contain super absorbent materials, i.e. materials in the form of fibres, particles, granulates, film etc, which have the ability to absorb liquid corresponding to several times the weight of the super absorbent material. The super absorbent material binds the absorbent fluid and in doing so, forms an aqueous gel. Furthermore, the absorption body 205 may comprise binding agents, shape stabilizing components, etc. Further absorbtion layers, which improve the absorption characteristics, may also be used, for example different kinds of liquid wicking inserts or layers of material. The absorption body 205 may be chemically or mechanically treated in order to alter the absorption characteristics. It is, for example, common to provide an absorption layer with compressed portions in order to direct the flow of liquid in the absorbtion body 205. Furthermore, other types of absorbing materials may be used, on their own, or in combination with cellulose fibres and super absorbent materials. Examples of possible absorbing materials are absorbing non-woven material, foam, etc.

On the outside of the liquid impermeable covering sheet 203, there is arranged an attachment element in the form of two areas 212 of self adhesive glue. Before use, the glue areas 212 are suitably covered with releasable protective layers of paper which have been treated with a release agent, or plastic film. The protective layers are not shown in the drawings. A number of other glue patterns than those shown are of course conceivable, as well as other kinds of attachment elements, such as for example Velcro fasteners, press buttons, girdles, special underwear, etc. A sanitary napkin of the kind shown in FIGS. 2 and 3, will during use be attached to the inside of a pair of regular underwear. In this application, the attachment element holds the sanitary napkin in place in the underwear during use. The attachment element should of course be of a kind that will permit the sanitary napkin to be removed from the underwear without causing damage to the underwear.

The sanitary napkin 201 is hour-glass shaped with wider end-portions 214,216 and a narrower crotch-portion 218 between the end-portions 214,216. The crotch-portion 218 is that part of the sanitary napkin which, during use, is intended to be positioned in the crotch of the user and serve as a receiving surface for body liquid which is secreted to the sanitary napkin. Furthermore, the sanitary napkin has two transverse end edges 220,222 and two longitudinal side edges 224,226 which extend between the end edges 220, 222.

The sanitary napkin 201 is further provided with fastening flaps 228,230, which are formed by the two covering sheets 202,203, and which protrude from the side edges 224,226 of the sanitary napkin 201 at the crotch-section 218. During use of the sanitary napkin, the fastening flaps 228,230 are intended to be folded around the leg edges of the underwear of the user and to be attached to the outside of the underwear. For this purpose, the fastening flaps 228,230 are provided with special attachment elements 232 which may be chosen in the same way as the attachment element 212 of the liquid impermeable covering sheet 203.

The liquid permeable covering sheet 202 consists of a first layer of material 208 and a second layer 209 of material. The first layer of material has a plurality of penetrating holes 204. The holes are arranged longitudinally on the sanitary napkin 201, in a band-shaped area which extends between the end edges 220,222, and has a width corresponding to the width of the absorbtion body 205 in the crotch-portion 218 of the sanitary napkin.

The first layer 208 of material is a textile material which, during use of the sanitary napkin, is intended to be in contact with the body of the user. The textile material may consist of a woven or knitted fabric, but is preferably a non-woven material of the spunbond type. The layer 208 of material consists at least in part of a material which is heat meltable. During the making of the holes 204 in the layer 208 of material, the heat meltable material has been melted in the area immediately adjacent to each hole 204. When the melted material has solidified after the hole making process, it forms a continuous, essentially liquid-tight edge 206 around the entire circumference of the hole 204. As mentioned previously, the continuous edge 206 increases the tensile strength of the covering material 202. Furthermore, the edge 206 prevents liquid from spreading from the holes 204 into the covering sheet 202. Instead, body fluid which strikes the sanitary napkin 201 will pass down through the covering layer 202 to the absorption body 205, which is positioned inside of the covering sheet.

The second layer 209 of material of the liquid permeable covering sheet 202 is arranged inside the first layer 208 of material. The second layer 209 of material is thus positioned between the first layer 208 of material and the absorption body 205 of the sanitary napkin. The second layer 209 of material consists of a material which is more hydrophilic than the first layer 208 of material, whereby transport of fluid between the two layers 208,209 of material takes place in the direction towards the absorption body 205 of the sanitary napkin. Examples of suitable materials are different types of non-woven materials, air laid or wet laid cellulose layers, different kinds of wadding, foam materials, etc.

In order to facilitate transfer of fluid between the fluid permeable covering layer 202 and the absorption body 205, the second layer 209 of material is suitably in direct contact with the absorption body 205. Preferably the layer of material is connected to the absorption body by means of glueing, welding, needling, etc.

FIG. 3 shows the second layer 209 of material as a separate layer, with the same width as the absorbing body 205. The two layers of material 208,209 in the covering sheet 202 are preferably connected to each other, for example by glueing, ultrasonically, or by needling. If the layers 208,209 of material are connected by means of needling, this is preferably done concurrently with the making of the holes 204 in the first layer 208 of material.

Although the second layer 209 of material has been shown as a separate layer, with a smaller extension across the sanitary napkin than the first layer 208 of material, it is of course possible to instead make the liquid permeable covering sheet 202 out of two or more layers of material with equal extensions. Such covering sheets may be formed by means of laminating the layers in question, or may consist of a single layer of material with an integrated layer structure.

It may be advantageous to make the liquid permeable covering sheet 202 with holes 204 of different sizes in different areas of the sanitary napkin, or with a different number of holes in different areas. For example, it is advantageous if the holes 204 in the area of the sanitary napkin 201, which will first be wet by excreted body fluid, are relatively large. In this way, a large quantity of fluid can be absorbed into the sanitary napkin in a short time. The covering sheet 202 further has the ability to let in high-viscosity components and protein particles which appear in menstrual fluid. For reasons of simplicity it is generally assumed that the part of the sanitary napkin which will initially be wetted is somewhere within the crotch-portion 218 of the sanitary napkin. Since large holes have a reduced ability to mask, or at least decrease the visual impression of the menstrual fluid which has been absorbed by the sanitary napkin, it is, however, desirable to limit the area with large holes 204 as much as possible. For this reason and since only a minor quantity of fluid is expected to pass into the sanitary napkin at the end-portions 214,216, the covering sheet 202 within these portions 214,216 suitably has holes 204 of a smaller dimension than at the crotch-portion 218. It is further more suitable if the holes 204 which are arranged along the side edges 224,226 of the sanitary napkins are fewer and/or have a smaller area than the centrally arranged holes 204. This reduces the risk that body fluid which has been absorbed by the sanitary napkin in the case of saturation of the absorption material will come out through the holes at the side edges 224,226.

Figure 4:
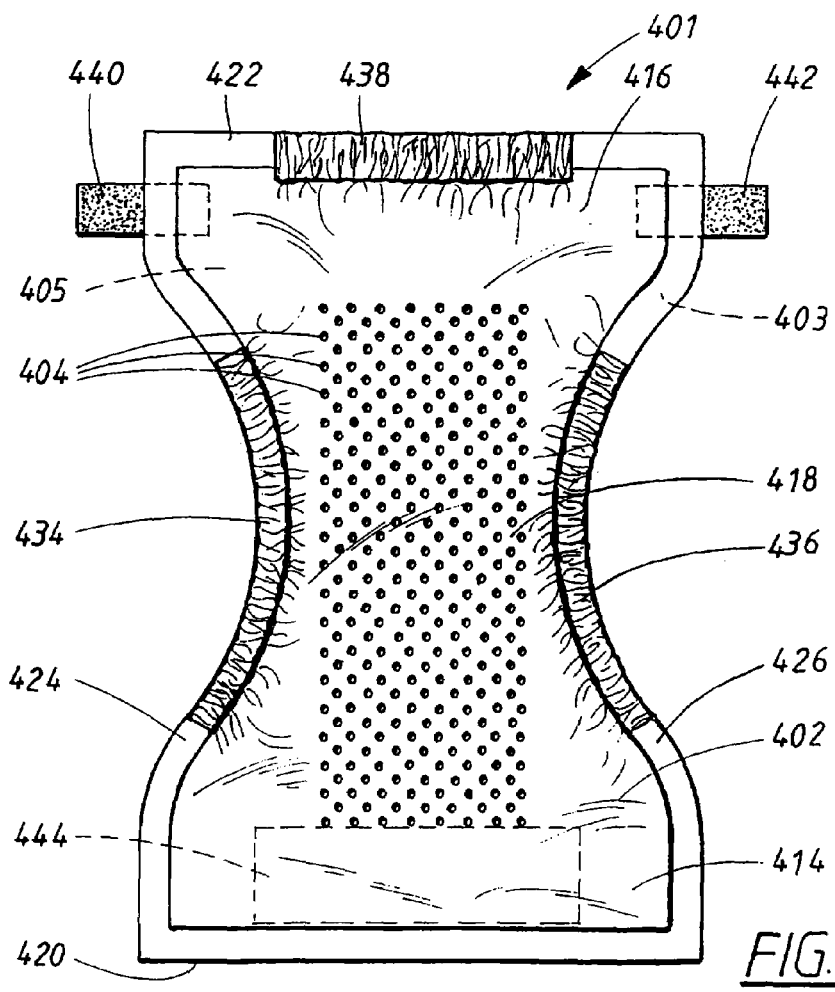
FIG. 4 shows a diaper with a liquid permeable covering layer according to the invention, seen from that side which during use is intended to face the user.

The diaper 401 of FIG. 4 has essentially the same principal construction as the sanitary napkin of FIGS. 2 and 3. Thus, the diaper 401 has an absorption body 405 enclosed between two covering sheets 402,403.

The absorption body 405 may be of any conventional kind. Examples of frequently used absorption materials are fluffed cellulose pulp, tissue layers, high absorbing polymers, absorbing foam materials, absorbing non-woven materials etc. Mixtures of materials, and absorption bodies constructed of layers of materials of different kinds and with different properties and different shapes are also possible.

The diaper 401 furthermore has two longitudinal side edges 424,426, a forward end edge 420 and a rear end edge 422 and has a front portion 414, a rear portion 416 and a thinner crotch-portion 418 between the front portion 414 and the rear portion 416.

Furthermore, elastic elements 434,436 are arranged along the side edges 424,426 of the crotch-portion 418 of the diaper. During use of the diaper, the elastic elements 434, 436, serve to keep the diaper in sealing contact around the legs of the user. A further elastic element 438 is arranged along the rear end edge 422 and is intended to give the diaper 401 a certain elasticity and to serve as a sealing means for the diaper around the waist of the user.

A tape tab 440,442 is attached to each side edge 424,426, close to the rear end edge 422. The tape tabs 440,442 constitute closing means for the diaper 401, to allow the diaper to be closed so that it will enclose the lower portion of a users torso, in a manner similar to pants. The tape tabs 440,442 co-operate with a receiving area 444 on the liquid impermeable covering sheet 403 of the diaper 401 at the forward section 414. The receiving area 444 can, for example, be in the form of a reinforcing material, which has been laminated to the liquid impermeable covering sheet 403. Thanks to the reinforcement, the diaper 401 may be closed and reopened without ruining the adhesion of the tape tabs 440,442 or ripping the liquid impermeable covering sheet 403.

Of course, many other types of closure means may be used instead of the described tape tabs 440,442. Examples of alternative closure means are Velcro fasteners, press studs, ribbons for tying etc.

As with the above described sanitary napkin, the liquid permeable covering sheet 402 comprises a perforated textile material according to the invention. The covering sheet 402 is, however, only perforated within a rectangular area centrally arranged on the diaper.

Figure 5:
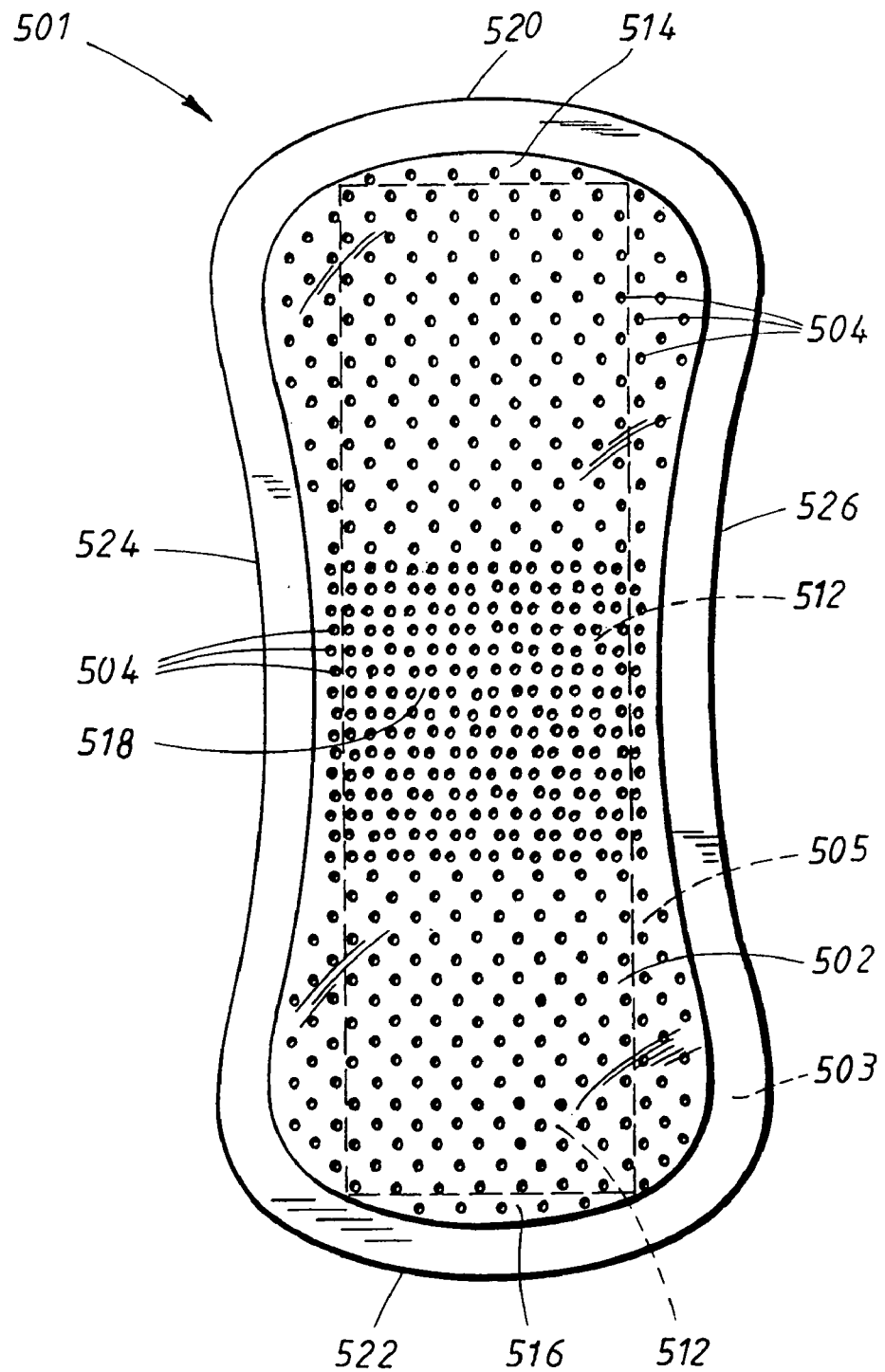
FIG. 5 shows an incontinence diaper with a liquid permeable covering layer according to the invention, seen from that side which during use is intended to face the user.

FIG. 5 shows an incontinence protector 501 which has a liquid permeable covering sheet 502 and a liquid impermeable covering sheet 503, which together enclose an absorption body 505.

Similar to the sanitary napkin 201 of FIGS. 2 and 3, the incontinence protector 501 is hourglass-shaped, with wider end-portions 514,516, and a thinner crotch-portion 518. The incontinence protector is limited in the plane by inwardly curved side edges 524,526, and outwardly curved end edges 520, 522.

The incontinence protector 501 is intended, during use, to be worn inside a pair of regular underwear. In order to fasten the incontinence protector inside the underwear, it is provided with a longitudinal rectangular area 512 of self-adhesive glue, arranged on the liquid impermeable covering sheet 503.

The liquid permeable covering sheet 502 is a covering sheet according to the invention, and thus has a plurality of penetrating holes 504, each hole being surrounded by a continuous, liquid-tight edge. The holes 504 are distributed across the entire surface of the incontinence protector, but with a greater density within the crotch-section 518 of the incontinence protector than at the end-sections 514,516. In this manner, the incontinence protector has a higher liquid permeability within that part which is intended to receive the majority of the body fluid which is secreted to the incontinence protector.

Figure 6:
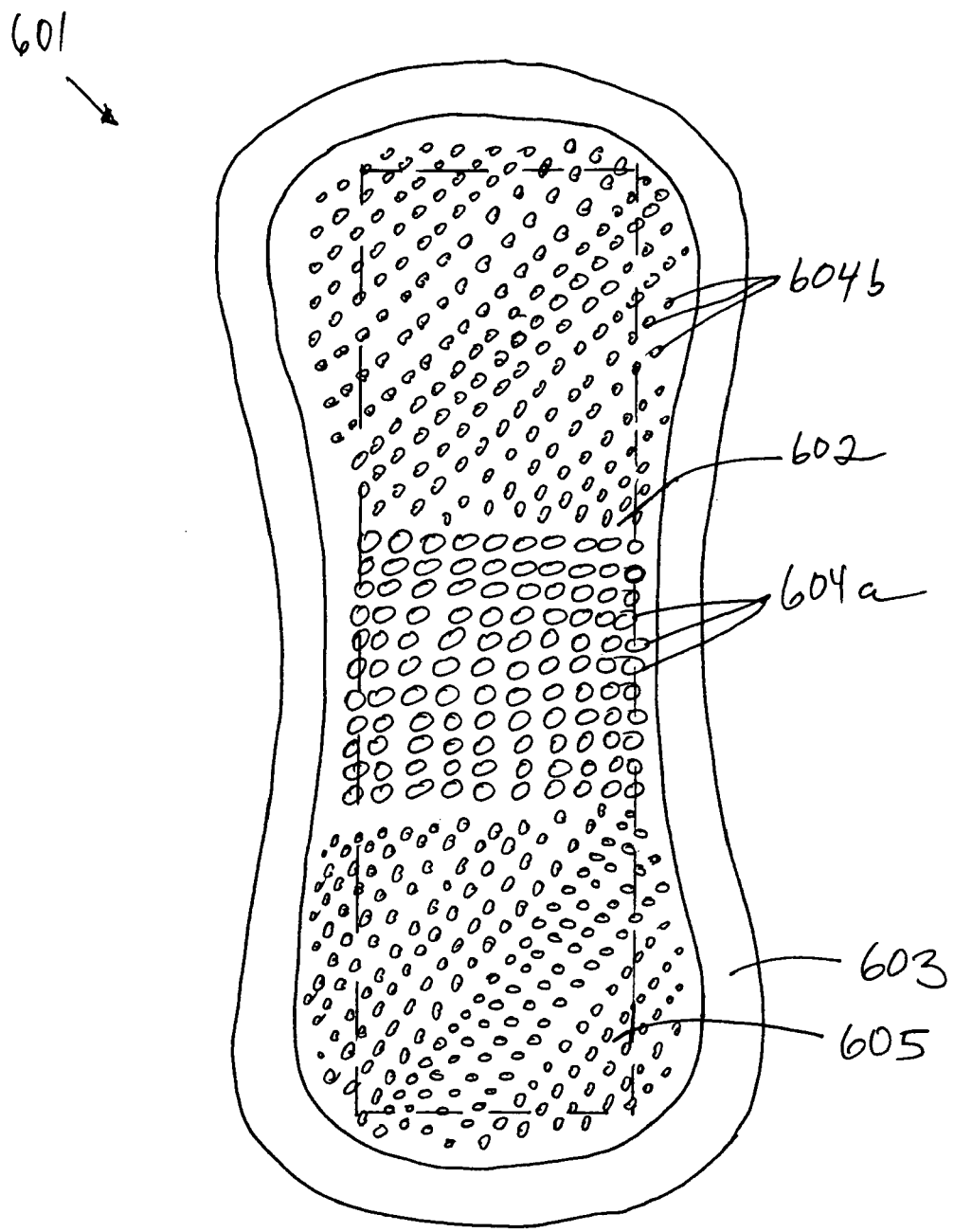
FIG. 6 shows an incontinence diaper with a liquid permeable covering layer according to the invention, seen from the side which during use is intended to face the user.

FIG. 6 shows an incontinence protector 601 which has a liquid permeable covering sheet 602 and a liquid impermeable covering sheet 603, which together enclose an absorption body 605. The liquid permeable covering sheet 602 has a plurality of penetrating holes. According to this embodiment, different areas of the covering sheet 602 have holes of different sizes. In particular, holes 604a arranged at the crotch portion have a larger surface area than holes 604b in the end portions of the covering sheet 602.

The invention is not limited to the above described embodiments, a number of further variations and modifications are possible within the scope of the appended patent claims.

The invention should also be regarded as comprising all possible combinations of the described embodiments.

What is claimed is:

1. A liquid permeable covering sheet for an absorbent article, comprising:
an apertured fibrous textile material, wherein the textile material comprises at least one thermoplastic component and that the covering sheet has a plurality of holes, each hole being surrounded by an essentially liquid impermeable edge which is formed by melting of the thermoplastic component in the vicinity of the holes;
wherein the covering sheet comprises at least two layers of material;
wherein the at least two layers of material comprise a first layer of material and a second layer of material, the second layer of material being more hydrophilic than the first layer of material.

2. The liquid permeable covering sheet according to claim 1, wherein the holes are formed by heated needles, and in that the liquid impermeable edges around the holes are formed at the same time as the holes.

3. The liquid permeable covering sheet according to claim 1, wherein the holes in the covering sheet are made ultrasonically.

4. The liquid permeable covering sheet according to claim 1, wherein the textile material is a non-woven material.

5. The liquid permeable covering sheet according to claim 1, wherein the covering sheet has holes of different sizes.

6. The permeable covering sheet according to claim 1, wherein it is laminated to a non-perforated liquid transfer layer.

7. The liquid permeable covering sheet according to claim 1, wherein the holes through the covering sheet have a liquid impermeable edge only in the first layer of material.

8. An absorbent article, comprising:
an absorption body enclosed in a covering sheet wherein at least one portion of the covering sheet consists of a liquid permeable covering sheet of a fibrous textile apertured material, wherein the textile material comprises at least one thermoplastic component and that the apertured covering sheet has a plurality of holes, each hole being surrounded by a liquid impermeable edge, wherein the liquid impermeable edge is formed by melting the thermoplastic component surrounding the holes in the immediate vicinity of the holes;
wherein the liquid permeable covering sheet comprises at least two layers of material;
wherein the at least two layers of material comprise a first layer of material and a second layer of material, the second layer of material being more hydrophilic than the first layer of material.

9. Absorbent article according to claim 8, wherein it has two end-portions, and a crotch-portion between the end portions, wherein the liquid permeable covering sheet has holes arranged at the crotch-portion which have a larger surface area than holes made in the covering sheet at either of the end-portions.

10. Absorbent article according to claim 8, wherein it has two longitudinal side edges wherein an edge area along each side edge has holes which are of a smaller dimension and/or are more sparsely arranged than holes arranged at the crotch-portion of the article inside the edge areas.

* * * * *